(12) United States Patent
Hain et al.

(10) Patent No.: US 8,127,591 B2
(45) Date of Patent: Mar. 6, 2012

(54) CALIBRATION FOR A NONDESTRUCTIVE MATERIAL TESTING SYSTEM

(75) Inventors: Stefan Hain, Effeltrich (DE); Hubert Mooshofer, Munich (DE); Fabricio De Carvalho Ferreira, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 432 days.

(21) Appl. No.: 12/407,164

(22) Filed: Mar. 19, 2009

(65) Prior Publication Data

US 2009/0288471 A1    Nov. 26, 2009

(30) Foreign Application Priority Data

Mar. 20, 2008  (DE) .......................... 10 2008 015 238

(51) Int. Cl.
*G01V 13/00*    (2006.01)
*G01N 29/04*    (2006.01)

(52) U.S. Cl. .......................................... 73/1.82; 73/641
(58) Field of Classification Search ................... 73/1.82, 73/1.84, 1.86, 641
See application file for complete search history.

(56) References Cited

U.S. PATENT DOCUMENTS

| | | | | |
|---|---|---|---|---|
| 3,962,671 A * | 6/1976 | Jilling | ............................ | 367/13 |
| 4,170,891 A | 10/1979 | Elsner | ............................ | 73/1.83 |
| 4,430,883 A * | 2/1984 | Auphan | ......................... | 73/1.83 |
| 4,476,549 A * | 10/1984 | Dragonette et al. | ............ | 367/13 |
| 5,077,908 A * | 1/1992 | Moore | ............................. | 33/550 |
| 5,319,683 A * | 6/1994 | Kurek et al. | .................... | 376/245 |
| 5,535,176 A * | 7/1996 | Yang | ............................... | 367/13 |
| 5,687,293 A * | 11/1997 | Snell | ............................. | 700/254 |
| 6,182,494 B1 | 2/2001 | Reed et al. | ..................... | 73/1.83 |
| 6,220,099 B1 | 4/2001 | Marti et al. | ..................... | 73/633 |
| 6,517,484 B1 * | 2/2003 | Wilk et al. | .................... | 600/437 |
| 2009/0282895 A1 * | 11/2009 | Hain et al. | .................... | 73/1.82 |

FOREIGN PATENT DOCUMENTS

| | | |
|---|---|---|
| EP | 0060952 A2 | 9/1982 |
| WO | 02/18958 A2 | 3/2002 |

OTHER PUBLICATIONS

Gunarathne, G.P.P., et al., "A Novel Technique for Dynamic Alignment of Ultrasonic Transducers in Real-Time Non-destructive Testing", School of Engineering, The Robert Gordon University, Aberdeen, AB10 1FR, UK, May 20, 2003.
German Office Action, German application No. 10 2008 015 238.2-523 pages, Sep. 29, 2008.
Zhu, Zhenqi et al. "Calibration of Laser Displacement Used By Industrial Robots," Optical Engineering, Bd. 43, Nr. 1 (2 pages).

* cited by examiner

*Primary Examiner* — J M Saint Surin
(74) *Attorney, Agent, or Firm* — King & Spalding L.L.P.

(57) ABSTRACT

Calibration for an ultrasonic nondestructive materials testing system is specified, the system having an array of ultrasonic transducers which can be linearly moved and pivoted. In order to compensate for the offset between the beam direction of the ultrasonic transducers and the rotation point of the pivoting system or another desired point of the transducers, this offset is determined using a calibrating body which is, for example, spherical.

20 Claims, 1 Drawing Sheet

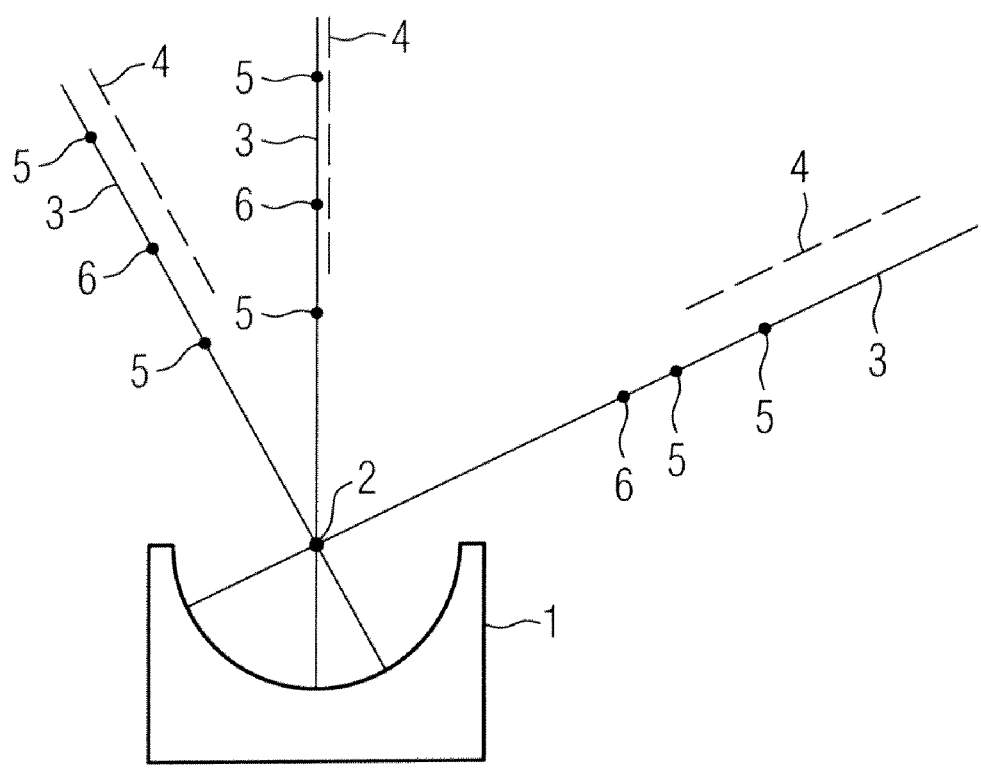

CALIBRATION FOR A NONDESTRUCTIVE
MATERIAL TESTING SYSTEM

CROSS-REFERENCE TO RELATED
APPLICATIONS

This application claims priority to German patent application No. 10 2008 015 238.2, filed Mar. 20, 2008. The complete disclosure of the above-identified priority application is hereby fully incorporated herein by reference.

TECHNICAL FIELD

The invention relates to the field of nondestructive materials testing. There are a number of possibilities for this. For example, sensors can be used to receive and evaluate radiation, for example thermal radiation, from a test specimen to be tested. In this case, the surface of the test specimen is scanned, for example. It is also possible to emit the radiation and to receive a reflected portion of this radiation again and evaluate it. The radiation may be electromagnetic radiation or else sound waves, for example ultrasound. In this case, the invention deals with an ultrasonic transducer system, in particular, but can also be used for other types of radiation. In the text below, the term transducer is used for a respective sensor or a combination of a sensor and an emitter for the radiation. For example, ultrasonic transducer may denote an ultrasonic sensor or a combination of an ultrasonic transmitter and an ultrasonic receiver.

BACKGROUND

Depending on the type of radiation used, it may be necessary to maintain a particular distance between the transducer or transducers and the surface of the test specimen. Furthermore, depending on the type of radiation used, it may be necessary to maintain a particular angle with respect to the surface of the test specimen. At least one pivoting system which can rotate the transducer or transducers about one or more pivot axes/rotation points is needed for this purpose in the case of curved surfaces, for example hemispherical ends of a rod.

Mechanical tolerances of the transducers themselves or those which occur when installing the transducers mean that a beam emitted by the transducers, for example an ultrasound beam, does not fall through the desired target point. One example of such a desired target point is the rotation point of the pivoting system. However, in terms of design, another rotation point which is not on the sound beam can also be selected for the pivoting system, and correspondingly displaced positioning (according to the design offset) can be carried out during pivoting. In this case too, the tolerances reduce the accuracy and prevent testing. The impingement point of the radiation is changed as a result even if, for example, only one of the pivot axes of the pivoting system is actuated. This reduces the accuracy of the materials testing or the materials testing is even made impossible.

In order to avoid this problem, it is known practice to insert the transducers into holders which are in mechanical contact with the surface of the test specimen. Runners or rollers ensure that the transducers follow the surface of the test specimen during movement and thus ensure the distance and angle. However, a prerequisite is that the curvature of the test specimen surface changes only slowly so that the mechanical system can follow the surface in a sufficiently accurate manner. However, the disadvantage of this solution is that the test specimen is exposed to a mechanical load. Furthermore, a certain amount of wear of the surface of the test specimen and a limited speed of the movement of the transducers result.

SUMMARY

According to various embodiments, a nondestructive materials testing device and a nondestructive materials testing method can be specified which are used to avoid the above mentioned problems.

According to an embodiment, in a nondestructive materials testing device comprising at least one transducer,
the transducer can be pivoted about a rotation point on at least one axis using a pivoting system,
the transducer can be linearly displaced in at least one direction using a linear movement system,
and the device is configured in such a manner that
a calibration value which specifies an offset between a desired point, which is in a desired beam direction of the transducer, and the actual beam direction of the transducer can be determined, and
the calibration value can be used to compensate for the offset in such a manner that a beam emitted by the transducer runs through the desired point.

According to a further embodiment, a calibrating body of a defined shape can be provided for the purpose of determining the calibration value. According to a further embodiment, the calibrating body may have at least part of a hollow-spherical, spherical, hollow-cylindrical or cylindrical surface. According to a further embodiment, the calibrating body can be a sphere or half of a hollow sphere. According to a further embodiment, the pivoting system and/or the linear movement system can be configured for rotation about two axes and for movement in 3 axes, respectively. According to a further embodiment, the calibration value can be used to control a beam from the transducer onto a workpiece to be tested in such a manner that the angle and the point at which said beam impinges on the surface of the workpiece can be varied independently of one another. According to a further embodiment, the transducer may be an ultrasonic transducer. According to a further embodiment, the device may have eight transducers.

According to another embodiment, a nondestructive materials testing method in which use is made of a nondestructive materials testing device having at least one transducer for emitting a beam may comprise the steps of—the transducer is moved over the surface of a workpiece to be tested using a pivoting system and a linear movement system,—a calibration value which specifies an offset between a desired point, which is in a desired beam direction of the transducer, and the actual beam direction of the transducer is determined, and—the calibration value is used to compensate for the offset in such a manner that a beam emitted by the transducer runs through the desired point.

According to a further embodiment, a calibrating body may be used to determine the calibration value, the offset being determined from the reflection of the beam by said calibrating body. According to a further embodiment, use can be made of a calibrating body having at least part of a hollow-spherical, spherical, hollow-cylindrical or cylindrical surface. According to a further embodiment, the beam may be directed onto the calibrating body from three different directions, and the linear displacement at which the beam reflected at the calibrating body strikes the transducer may be determined for each of the directions. According to a further embodiment, the linear displacement at which the beam reflected at the calibrating body strikes the transducer may be determined for each of the directions for two distances between the transducer and the calibrating body.

According to another embodiment, the method may use a device as described above.

BRIEF DESCRIPTION OF THE DRAWINGS

Further advantages and details of the invention are explained using the exemplary embodiment illustrated in the drawing.

The FIGURE schematically shows a hollow-spherical calibrating body 1 and the measurement points 5 and directions used by way of example to determine the offset.

DETAILED DESCRIPTION

In the nondestructive materials testing device according to an embodiment, having at least one transducer, the transducer can be pivoted about a rotation point on at least one axis using a pivoting system. Furthermore, the transducer can be linearly displaced in at least one direction using a linear movement system. The device is also configured in such a manner that a calibration value which specifies an offset between a desired point, which is in a desired beam direction of the transducer, and the actual beam direction of the transducer can be determined, and the calibration value can be used to compensate for the offset in such a manner that a beam emitted by the transducer runs through the desired point. In this case, the offset is understood as meaning the minimum distance between the beam from the transducer and the desired point, the beam being considered in an idealized manner without its widening. The desired point may be, in particular, the rotation point of the pivoting system.

As a result of its features, the device according to an embodiment is able to compensate for the inaccuracies, caused by mechanical tolerances, when irradiating, and when receiving echoes from, the surface of a workpiece or test specimen and is thus able to carry out considerably more accurate testing. In particular, it is able to vary the impingement angle of the radiation emitted by the transducer independently of the impingement point of the radiation. That is to say, the impingement angle can be changed, while the impingement point remains the same. Conversely, the impingement point can be changed without the impingement angle being changed by the machine; the impingement angle is therefore then dependent only on the curvature of the test specimen.

A calibrating body is advantageously provided for the purpose of determining the calibration value. Said body preferably has a hollow-spherical or spherical surface, that is to say is half of a hollow sphere or a sphere, in particular. A hollow-cylindrical or cylindrical surface can also be used, which is expedient, in particular, when the pivoting system allows only rotation about one axis.

The pivoting system and/or the linear movement system is/are configured for rotation about two axes and for movement in 3 axes, respectively. The transducer is preferably an ultrasonic transducer which is a combination of an ultrasonic emitter and a sensor for ultrasound. The device preferably has a plurality of transducers, in particular eight transducers.

In the nondestructive materials testing method according to an embodiment, use is made of a nondestructive materials testing device having at least one transducer for emitting a beam. Furthermore, the transducer is moved over the surface of a workpiece to be tested using a pivoting system and a linear movement system. A calibration value which specifies an offset between a desired point, which is in a desired beam direction of the transducer, and the actual beam direction of the transducer is determined. The calibration value is finally used to compensate for the offset in such a manner that a beam emitted by the transducer runs through the desired point.

The result of the procedure according to various embodiments is thus the determination of a set of parameters comprising at least one parameter which allows the desired movement to be converted into an actual movement. For example, a height correction may additionally be carried out in the case of a slightly oblique but essentially perpendicular axis of rotation. The offset can thus be detected and compensated for in a plurality of dimensions.

The beam is preferably directed onto the calibrating body from three different directions, and the linear displacement at which the beam reflected at the calibrating body strikes the transducer is determined for each of the directions. In this case, it is advantageous for a high level of accuracy if the linear displacement at which the beam reflected at the calibrating body strikes the transducer is determined for each of the directions for two distances between the transducer and the calibrating body. The propagation time is determined from the two points and a point at a defined distance is determined by means of interpolation.

The position of the sound beam from an ultrasonic transducer relative to the mechanical rotation point 7 is gauged using a calibrating apparatus and the associated measurements according to the steps outlined below. If this difference is known, a linear movement system for the transducer can be used to carry out a compensating movement when the pivoting angle changes and the point at which the sound beam impinges on a test specimen remains independent of the angle of incidence.

In this example, the calibrating apparatus has a calibrating body 1 in the form of a hollow-spherical section. As a result, the calibrating body 1 reflects only those sound beams which run through the center point 2 of the calibrating body 1 back to the transducer. A coordinate point is then known for each beam of this type. In order to determine the coordinates of the rotation point 7, 3 pivoting angles, that is to say directions for irradiating the calibrating body 1, are now initially set, thus resulting in three sound beams without alignment 4. The coordinates specified by the linear movement system in this case are known. Positions 5 in which the sound beams run back to the transducer, that is to say through the center point 2 of the calibrating body 1, are sought for each of the pivoting angles at two different distances by varying the transducer using the linear movement system. The distance between the positions 5 and the center point 2 is determined by the sound propagation times.

Three interpolated points 6, which are on a circle around the center point of the calibrating body 1, that is to say are at the same distance from the center point 2, are then inferred from the six positions 5 by means of interpolation. The position of the center point 2 can be determined from the coordinates of the interpolated points 6. The position of the rotation point 7 can be determined together with the linear displacements used to respectively align the beams from the transducer with the center point 2 and the coordinates of the center point 2 itself.

What is claimed is:

1. A nondestructive materials testing device comprising at least one transducer, wherein
the transducer is operable to be pivoted about a rotation point on at least one axis using a pivoting system,
the transducer is operable to be linearly displaced in at least one direction using a linear movement system, And wherein the transducer is configured in such a manner that
- a calibration value which specifies an offset between a desired point, which is in a desired beam direction of the transducer, and the actual beam direction of the transducer is determined, and
- the calibration value is usable for compensating for the offset in such a manner that a beam emitted by the transducer runs through the desired point.

2. The device according to claim 1, wherein a calibrating body of a defined shape is provided for the purpose of determining the calibration value.

3. The device according to claim 2, wherein the calibrating body has at least part of a hollow-spherical, spherical, hollow-cylindrical or cylindrical surface.

4. The device according to claim 3, wherein the calibrating body is a sphere or half of a hollow sphere.

5. The device according to claim 1, wherein at least one of the pivoting system and the linear movement system is/are configured for rotation about two axes and for movement in 3 axes, respectively.

6. The device according to claim 1, wherein the calibration value is usable for controlling a beam from the transducer onto a workpiece to be tested in such a manner that the angle and the point at which said beam impinges on the surface of the workpiece is varied independently of one another.

7. The device according to claim 1, wherein the transducer is an ultrasonic transducer.

8. The device according to claim 1, wherein the device comprises eight transducers.

9. A nondestructive materials testing method in which use is made of a nondestructive materials testing device having at least one transducer for emitting a beam, the method comprising the steps of:
- moving the transducer over the surface of a workpiece to be tested using a pivoting system and a linear movement system,
- determining a calibration value which specifies an offset between a desired point, which is in a desired beam direction of the transducer, and determining the actual beam direction of the transducer, and
- using the calibration value to compensate for the offset in such a manner that a beam emitted by the transducer runs through the desired point.

10. The method according to claim 9, wherein a calibrating body is used to determine the calibration value, the offset being determined from the reflection of the beam by said calibrating body.

11. The method according to claim 10, wherein use is made of a calibrating body having at least part of a hollow-spherical, spherical, hollow-cylindrical or cylindrical surface.

12. The method according to claim 9, wherein the beam is directed onto the calibrating body from three different directions, and the linear displacement at which the beam reflected at the calibrating body strikes the transducer is determined for each of the directions.

13. The method according to claim 12, wherein the linear displacement at which the beam reflected at the calibrating body strikes the transducer is determined for each of the directions for two distances between the transducer and the calibrating body.

14. The method according to claim 9, further comprising the steps of
- using a device comprising at least one transducer, wherein the transducer is pivoted about a rotation point on at least one axis using a pivoting system, and wherein the transducer is linearly displaced in at least one direction using a linear movement system, and
- configuring the device in such a manner that a calibration value which specifies an offset between a desired point, which is in a desired beam direction of the transducer, and the actual beam direction of the transducer is determined, and the calibration value is usable for compensating for the offset in such a manner that a beam emitted by the transducer runs through the desired point.

15. The method according to claim 14, wherein a calibrating body of a defined shape is provided for the purpose of determining the calibration value.

16. The method according to claim 15, wherein the calibrating body has at least part of a hollow-spherical, spherical, hollow-cylindrical or cylindrical surface.

17. The method according to claim 16, wherein the calibrating body is a sphere or half of a hollow sphere.

18. The method according to claim 14, wherein at least one of the pivoting system and the linear movement system is/are configured for rotation about two axes and for movement in 3 axes, respectively.

19. The method according to claim 14, wherein the calibration value is usable for controlling a beam from the transducer onto a workpiece to be tested in such a manner that the angle and the point at which said beam impinges on the surface of the workpiece is varied independently of one another.

20. The method according to claim 14, wherein the transducer is an ultrasonic transducer.

* * * * *